United States Patent [19]

Herrmann et al.

[11] Patent Number: 5,989,880
[45] Date of Patent: Nov. 23, 1999

[54] METHOD OF PREPARING LYSOZYME DIMERS

[75] Inventors: Peter Herrmann; Peter Klein, both of Itingen, Switzerland

[73] Assignee: Nika Health Products Ltd., Liechtenstein, Liechtenstein

[21] Appl. No.: 08/197,647

[22] Filed: Feb. 16, 1994

Related U.S. Application Data

[62] Division of application No. 07/867,706, filed as application No. PCT/US90/00140, Jan. 8, 1990, Pat. No. 5,314,816.

[51] Int. Cl.$^6$ .............................. C12N 9/36; A61K 37/48
[52] U.S. Cl. ............................................. 435/188; 435/206
[58] Field of Search ...................................... 435/188, 206

[56] References Cited

U.S. PATENT DOCUMENTS

| | | | |
|---|---|---|---|
| 3,915,798 | 10/1975 | Yamaguchi et al. | 435/180 |
| 3,941,655 | 3/1976 | Heady et al. | 435/234 |
| 4,371,612 | 2/1983 | Matsumoto et al. | 435/181 |
| 4,705,755 | 11/1987 | Hasegawa et al. | 435/206 |
| 4,805,702 | 2/1989 | Waite | 930/10 |
| 4,959,309 | 9/1990 | Dattagupta et al. | 435/188 |
| 4,966,851 | 10/1990 | Durance et al. | 435/206 |
| 5,200,182 | 4/1993 | Kiczka | 435/199 |

FOREIGN PATENT DOCUMENTS

| | | | |
|---|---|---|---|
| 1221046 | 4/1987 | Canada | 435/206 |
| 0071490 | 5/1980 | Japan | 435/206 |
| 3233787 | 4/1988 | Japan | 435/206 |

OTHER PUBLICATIONS

CA95–093078(11) Hashimoto Shvichi et al Int. J. Radiat. Relat Stud Phys Chem Med 40(1) 1981 31–46.
CA89–370550/50 Kicizka ABS WO8911294 (Nov. 30, 1989) Equivalence U.S. 5200182.
CA097–019873(03) Hashimoto Shivichi et al Int. J. Radia Relat. Stud. Phys. Chem. Med 41(3) 1982 303–14.
CA096–213251 (25) Sorrentino Salvatore et al Eur J. Biochem 124 (1) 1982 pp. 183–189.
Sorrentino et al Eur. J. Biochem 124(1) 1982 pp. 183–189.
Eur. J. Biochem., vol. 124, 1982, Sorrentino: "Dimerization of Deoxyribonuclease I, Lysozyme and Papain", see p. 184, line 17 —line 22; p. 184, line 47—line 57.
Chemical Abstracts, vol. 84, No. 15, Apr. 12, 1976 (Columbus, Ohio US), Wang et al.: "Preparation of Cross–Linked Dimers of Pancreatic Ribonuclease", see p. 241, Abstract 10156x, & Biochemistry 1976, 15(3), 660–5.
Chemical Abstracts, vol. III, No. 13, Sep. 25, 1989, (Columbus, Ohio), Roth Mary R. et al.: "Analysis of Dimeric Species Derived From The Reaction of Phosphatidylethanolamine with Dimethylsuberimidate", see p. 360, abstract 111947u, & Chem. Phys. Lipids 1989, 51(1), 39–46.
Chemical Abstracts, vol. 97, No. 3, Jul. 9, 1982, (Columbus, Ohio), Hashimoto Shuichi et al.: "Dysozyme Dimer Formation On Lysozyme Oxidation With BR2", see abstract 19873M, & Int. J. Radiat. Biol. Rela. Study. Phys., Chem. 1982, 41(3), 303–14.

*Primary Examiner*—Herbert J. Lilling
*Attorney, Agent, or Firm*—Ostrolenk, Faber, Gerb & Soffen, LLP

[57] ABSTRACT

A method is provided for preparing a highly purified lysozyme dimer product which comprises dimerizing the lysozyme monomer with a suberimidate coupling reagent in a buffer solution adjusted to pH 10, stopping the dimerization at a given point by lowering the pH to 7 via addition of HCl or other suitable acid solution, and purifying the dimeric lysozyme by a series of elution steps carried out using ion exchange resin column chromatography. Monomeric lysozyme remaining undimerized by the initial dimerization step is recycled into the process in order to increase yield. The present system is advantageous in that large amounts of purified lysozyme dimer can be prepared efficiently and relatively inexpensively, and the lysozyme dimer so produced is useful in treating viral and/or bacterial diseases without causing the cytotoxic effects associated with the lysozyme monomer.

2 Claims, 2 Drawing Sheets

METHOD OF PREPARING LYSOZYME DIMERS

This is a division of application Ser. No. 07/867,706, filed Jul. 8, 1992 and now U.S. Pat. No. 5,314,816 which was the national stage filing of PCT/US90/00140 filed Jan. 8, 1990.

FIELD OF THE INVENTION

The invention relates to a series of techniques used to prepare and purify a lysozyme dimer which will be particularly useful in the treatment of viral and bacterial infections.

BACKGROUND OF THE INVENTION

The ever growing number of bacterial strains and viral diseases which are resistant to antibiotics have made it necessary to introduce new kinds of drugs in order to treat humans and animals. Among the many present treatments and medicines used, it has been known to administer enzymes in monomeric form in order to benefit patients afflicted with various diseases. Enzymes are catalytically active proteins which perform almost all major life processes in organisms. Thus, many enzymes, either individually or in certain combinations, have been isolated for their physiochemical, physiological, or biological effects.

Among the various enzymes for which certain therapeutic effects have been documented, it is presently known that lysozyme, which has been known since 1922, can be used in various physiological and biological treatments. It has been observed that lysozyme has various therapeutic properties, such as antiviral, antibacterial, anti-inflammatory and antihistaminic effects. The antibacterial effect of lysozyme appears to be based on the hydrolysis of the beta-1-4-glycoside bond between n-acetylomuraminic acid and n-acetyloglucosamine, both contained in the bacterial wall.

Unfortunately, the tremendous potential with regard to beneficial effects possible through use of lysozyme has not been achieved primarily due to the observed cytotoxic effect of the monomeric form of this enzyme. For example, in tests with cultured fibroblasts, there has been an observed cytotoxic effect from doses of lysozyme in monomeric form even when administered at very small quantities. It thus became necessary to develop a way to maximize the potential beneficial effects which could be obtained from lysozyme by finding an effective way of controlling the cytotoxic effects associated with the monomer.

It has recently been discovered that an antiviral or antibacterial composition which does not exhibit cytotoxic effects can be constructed from lysozyme if one prepares a composition based on the dimeric form of the enzyme. Use of lysozyme in the dimeric form results in a composition useful in the treatment of a number of infectious diseases yet which does not exhibit the highly cytotoxic effects normally associated with the lysozyme monomer. The use of lysozyme dimer in various therapeutic treatments is disclosed in a co-pending application, PCT Application US88/01785.

Although ways of manufacturing the dimeric form of lysozyme from its monomeric form are known, it is now imperative that one be able to produce large amounts of the dimeric form in an inexpensive and efficient manner. It is thus highly desirable to develop a system for producing and testing great amounts of purified lysozyme dimer which does not contain the monomeric or multimeric form of the enzyme, or other contaminants.

SUMMARY OF THE INVENTION

In accordance with the present invention, an efficient method of preparing a purified lysozyme dimer product is provided which comprises the steps of:

a) preparing a lysozyme solution by adding monomeric lysozyme to a buffer solution adjusted to a pH of at least about 9;

b) adding a suberimidate coupling reagent such as dimethyl suberimidate in order to dimerize the lysozyme monomers in the solution while the solution is kept at a pH at or above about 9;

c) lowering the pH to about 7 in order to stop the dimerization reaction at a given point;

d) purifying the dimerized lysozyme solution by carrying out a first elution step in which the solution is eluted through an ion exchange column, and fractions which are substantially comprised of the dimeric form of lysozyme are collected;

e) filtering the collected fractions from the first elution step by carrying out a second elution step in which the collected fractions from the first elution step are eluted through an ion exchange column; and f) collecting the highly purified dimeric lysozyme product resulting from the second elution step.

In the above way, great amounts of purified lysozyme dimer can be manufactured which will be useful in treating a variety of viral and bacterial diseases.

BRIEF DESCRIPTION OF THE DRAWING FIGURES

DETAILED DESCRIPTION OF THE PREFERRED EMBODIMENTS

Figure 1:
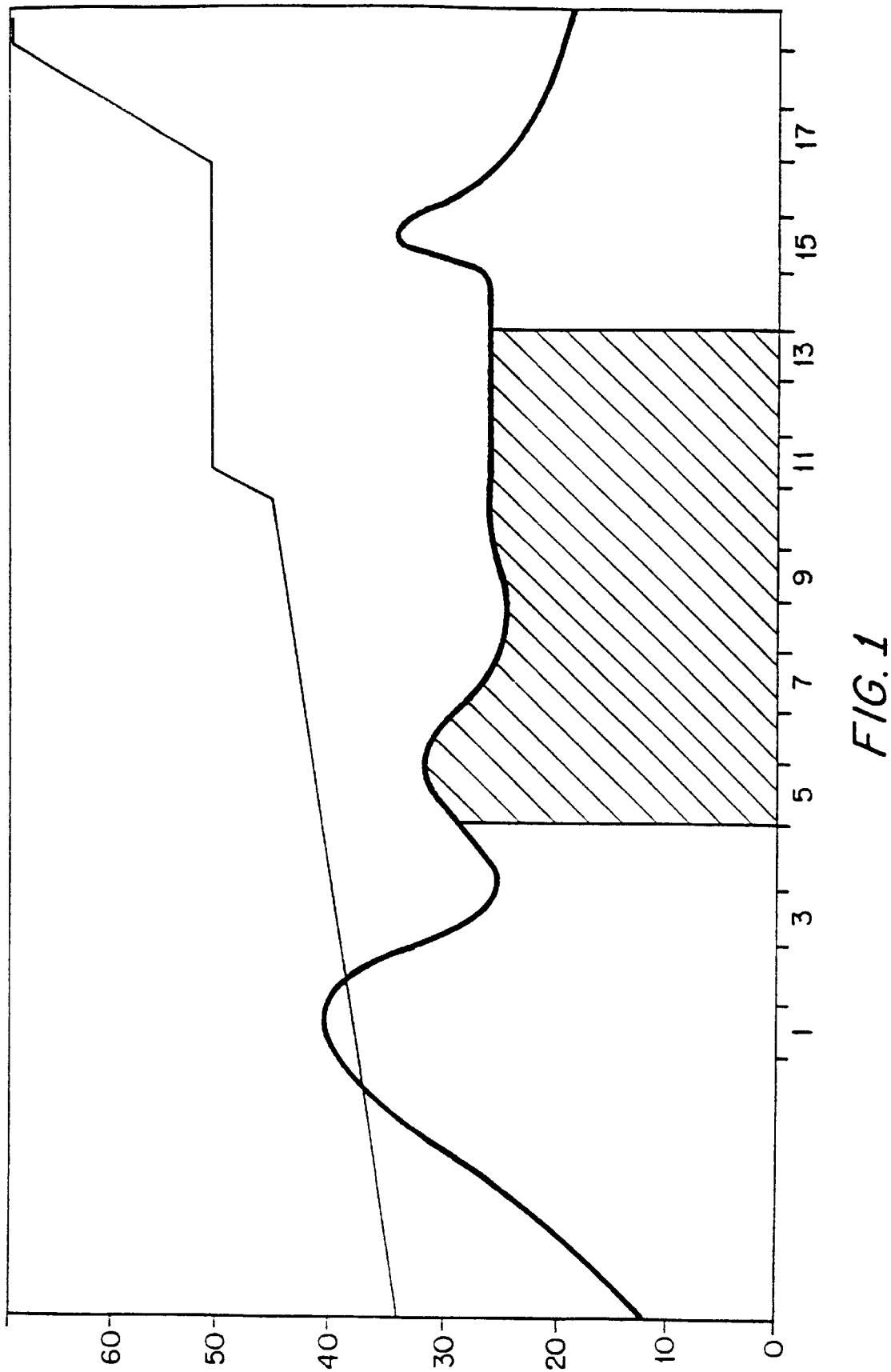
FIG. 1 is a graphic representation of the elution profile obtained from the first elution step carried out in accordance with the present invention.

In preparing lysozyme dimers in accordance with the present invention, any currently available lysozyme monomers can be used as the starting materials. In the present invention, the lysozyme monomers used were obtained from Serva Feine Biochemica, GmbH, Heidelberg, and had Catalog No. 28260. Before a coupling reagent is added to the monomer, a lysozyme solution is prepared in a beaker by dissolving the monomer in a phosphate buffer solution at room temperature while continuously stirring the solution for at least about two hours. The phosphate buffer solution employed s preferably an 0.1 M disodium hydrogen phosphate dihydrate buffer. A suitable buffer solution has been prepared by dissolving about 70 grams of disodium hydrogen phosphate dihydrate in about 1,000 ml $H_2O$. Although actual amounts of the reagents and solutions used in the present invention can vary, the dimerization reaction of the present invention has been carried out using from about 40 to about 60 grams of the lysozyme monomer which has been dissolved in a beaker having about 5 liters of the disodium hydrogen phosphate dihydrate buffer. It is also preferred that the monomeric solution be adjusted to have a pH of at least about 9, and most preferably about 10. The pH adjustment can be made using a basic solution such as 1 N NaOH.

The dimerization reaction is then allowed to take place by adding a suitable suberimidate coupling reagent in proportion to the lysozyme monomer solution while maintaining the pH at or above about 9. It is preferred that a dimethyl suberimidate coupling reagent be used in the present invention. To the solution prepared as indicated above, 4–6 grams of the dimethyl suberimidate is added to the monomer solution and will dissolve within about one minute. The coupling reaction is allowed to take place for about 60 minutes at room temperature (25+/−5° C.) while the solution is continuously stirred with a magnetic or other stirrer.

The dimerization reaction can be stopped at a given point by lowering the pH to about 7 (±0.2), and this can be accomplished with the addition of 1 M HCl and/or the addition of a 0.2 M ammonium acetate solution (roughly about 250 ml). A suitable ammonium acetate solution has been prepared using about 15 grams dissolved in 1,000 ml $H_2O$. Normally, the dimerization reaction is allowed to go for about 1 hour, although greater or lesser periods of time before the reaction is stopped may be allowed depending on the precise amounts and nature of the reagents and solutions used.

It is preferred at this point that the entire reaction mixture, which generally shows great turbidity, be passed through a membranous filter in order to separate off undissolved particles. This is usually necessary because the solution at this point will contain a portion of multimers which are present in undissolved form. To separate out multimers and other undissolved particles, a filter of about 0.4–0.5 $\mu$m pore size is preferred for use in this step.

Gel electrophoresis studies have been carried out on samples taken at different times following the addition of the coupling regent to the lysozyme monomer solution. These studies show that although the monomer form is clearly visible in almost every fraction analyzed, a band corresponding to the dimeric form of the lysozyme is recognizable after about 10 minutes of reaction time, and the band grows larger as the reaction continues. The monomeric weight of lysozyme is approximately 14,000, and the dimeric band corresponds to a size of about 30,000 in molecular weight. In the electrophoretic traces, the generation of multimeric forms can also be recognized.

In order to prepare substantial amounts of purified lysozyme dimer product, it is preferred that the dimerized lysozyme solution undergo at least two further purification steps in order to isolate the lysozyme dimers and remove lysozyme monomers or other contaminants. The removed undimerized lysozyme monomers can be collected and are preferably recycled in the present invention so as to further maximize efficiency in the production of dimers.

A first purification step is preferably carried out using ion exchanger chromatography. In this step, the dimerized lysozyme solution obtained through the dimerization process described above is introduced into an ion exchange resin column comprised of Sepharose or other cation exchange materials. In the preferred embodiment, a column of S-Sepharose FF (Pharmacia) of approximately 10 cm in diameter and 25 cm in height is packed with a volume of about 2.1 liters equilibrated with 4.2 liters of a 50 mM K-phosphate buffer solution at pH 7. Approximately 5 liters of the dimerized solution is applied to the ion exchanger column, and elution will preferably take place at a flow rate of about 60 ml/minute. It is also preferred that the elution will take place using a salt gradient of 0.15–1 M NaCl in the 50 mM K-phosphate buffer. Fractions from this elution step are collected and held in sterile flasks by use of a device such as a fraction collector (LKB 2211 Suprec). An elution profile can be recorded by means of an LKB 2210 recorder, which runs at a velocity of 1 mM/minute, and this elution profile can be used in determining the precise composition of the fractions collected. The absorption of the collected solutions are preferably measured at 280 nm by means of an LKB 2238 UVICOR S II.

The precise protein content of each of the fractions collected from the first elution step described above are preferably analyzed by a gel electrophoresis method such as the SDS-PAGE (SDS-polyacrylamide gel electrophoresis) technique such as described in Thomas et al, PNAS 72: 2626 (1979). In this electrophoretic study, preferably about 50 $\mu$l of each fraction is mixed with about 50 $\mu$l of a coating buffer and the mixture is heated for a period of about 10 minutes at about 95° C. Next, 25 $\mu$l of this mixture is spread into a gel pocket. After electrophoresis is carried out for approximately 4 hours at 20–35 mA, the protein bands separate out and are preferably made visible by coloring with a dye such as Coomassie-Blue R250 (Merck).

Using the SDS-gel process, monomers, dimers and multimers of lysozyme can be separated out. The electrophoretic studies can be used to identify those collected lysozyme fractions which are mostly in the dimeric form. The fractions which are substantially comprised of the lysozyme dimers are collected, and are preferably concentrated down to about 800 ml in a tangential flow system.

At this point, it is preferred that a subsequence iltering step be carried out to further ensure the purification of the dimer product. In the preferred embodiment, the collected fractions from the first elution step which have been concentrated using the tangential flow system, will be eluted again through an ion exchange column. It is contemplated that a column such as a Sephadex G 50 F (Pharmacia) of approximately 25 cm in diameter and 120 cm in height will be employed. The column is equilibrated with a volume of about 60 liters of a 5 mM ammonium acetate buffer solution which sets the pH at around 5. A suitable ammonium acetate buffer solution was prepared using about 4 grams of ammonium acetate dissolved in 1,000 ml of water adjusted to a pH of about 5 with a solution of 3 grams of acetic acid in approximately 1,000 ml of distilled water.

The lysozyme dimer solution collected from the first elution step, which has been concentrated by a tangential flow system, is-coated onto the ion exchange column so that elution preferably takes place at a flow rate of about 70 ml/minute in the equilibrium buffer. As in the above first elution step, fractions are collected and stored, and approximately 50 $\mu$l of each fraction is analyzed by the SDS-PAGE techniques discussed above. In addition, the elution profile is again recorded using a recorder running at a velocity of about 0.5 mm/minute. The absorption again is measured at 280 nm. Elution profiles obtained from fractions taken after the second elution step still show three peaks, but the profiles are primarily comprised of a middle peak which represents the lysozyme dimer fractions. By this point, there remains only minimal amounts of multimeric and monomeric forms of the lysozyme. The highly purified dimer fractions as indicated from the middle peaks of the elution profile are then collected, and once again are preferably concentrated using a tangential flow system. Ultimately, the purified dimers are lyophilized and stored until needed.

This total process can be repeated as often as necessary until the desired volume of final dimer product is obtained. Individual dimer batches after purification can be placed in distilled water and further lyophilized. In this way, a homogenous charge of lysozyme dimer can be obtained which will be highly useful in the treatment of many viral and bacterial diseases. In addition to its antiviral and antibacterial effects, other therapeutic benefits such as anti-inflammatory and antihistaminic properties have been attributed to the use of lysozyme dimer, all without the cytotoxic effects associated with the lysozyme monomer. The present method is thus useful in efficiently producing large amounts of the purified beneficial lysozyme dimer product. Because of its effect in decomposing bacteria, the dimer product produced by the present invention can be tested for effectiveness by administering the dimer to a microorganism solution and subsequently monitoring the decrease in the level of microorganisms (as measured using a spectral photometer) after the enzyme dimer has been applied. Tests conducted in this manner have indicated that the lysozyme dimers produced using the method of the present invention have a great potential for combatting viral and bacterial diseases.

The following examples are presented as illustrative of the present invention and are not intended to limit its scope in any way:

EXAMPLE 1
Preparation of Lysozyme Dimer 50 grams of lysozyme monomer (Serva Feine, Catalog No. 28260) were dissolved in a covered beaker using 5 liters of a 0.1 M disodium hydrogen phosphate dihydrate buffer which was continuously stirred for 2 hours at 25° C. The phosphate dihydrate buffer was prepared using 70.98 g disodium hydrogen phosphate×$2H_2O$ (Merck, p.A.) dissolved in 1,000 ml $H_2O$. The pH of the solution was adjusted to 10 using 1 N-NaOH. Next, 5 grams of the coupling reagent dimethyl suberimidate (Sigma) was added to the protein solution, and the pH was continually readjusted to pH 10. The reagent completely dissolved within 1 minute, and the coupling reaction was incubated for 60 minutes at room temperature (25° C.) with continuous stirring using a magnetic stirrer. The reaction was stopped by lowering the pH to 7 using 1 M HCl and about 250 ml of an 0.2 M ammonium acetate solution. The 0.2 M ammonium acetate solution was prepared using 15.42 g ammonium acetate (Merck, p.A.) dissolved in 1,000 ml $H_2O$. The entire reaction mixture showed great turbidity at this point, and was then passed through a membranous filter of 0.45 μm pore size in order to separate off undissolved particles. The undissolved particles included multimers which were present in the undissolved form, as detected by means of an SDS-gel-electrophoresis.

Following addition of the coupling regent, samples were taken at different times and were analyzed by gel electrophoresis. The monomeric form of lysozyme was clearly visible in every trace recorded. It was represented by a lower band running at a relative molecular weight of about 14,000 (molecular weight of lysozyme is 14,386). From the second trace on, taken at about 10 minutes reaction time, the dimeric double band could be observed, and this band grew larger as the reaction continued. The dimeric band corresponded to a size of about 30,000 in molecular weight. Additionally, in the later traces, a multimeric band could also be recognized.

In order to produce a preliminary purification of the product, 5 liters of the above composition was introduced through a cation exchanger comprised of a column of S-Sepharose FF (Pharmacia). The column, 10 cm in diameter and 25 cm in height, had a volume of 2.1 liters equilibrated with 4.2 liters of 50 mM K-phosphate buffer at pH 7. The 5 liters of the dimerized solution was coated onto the column and eluted at a flow rate of 60 ml/minute in a gradient of 0.15–1 m NaCl in 50 mM of K-phosphate buffer at pH 7.

The salt gradient was established and controlled in the following manner using as a gradient-mixer an LXB 2152 Controller. A first solution (Solution A) was prepared which comprised 50 mM K-phosphate buffer pH 7 with 0% NaCl, and a second solution (Solution B) was prepared comprising 50 mM of K-phosphate buffer pH 7 and 1 M NaCl. At the starting time (t0), the proportion of Solution B in the elution buffer is 15%; after one hour (t1), it rises directly to 50%, which is reached after 3.5 hours (t4.5), and is maintained for 30 minutes (t5). Within one subsequent hour (t6) it rises to 100% and remains constant for one hour (t7). Then it drops within 5 minutes (t7.05) back again to approximately 0%. The column is next washed for 90 minutes (t8.35) with a 0% NaCl portion.

From the elution in the S-Sepharose cation exchanger, fractions of approximately 600 milliliters, resulting from accumulation corresponding to 10 minutes-from the eluted flow, are collected in sterile 2 liter Schott flasks. The collection is carried out by means of a fraction collector (LKB 2211 Suprec). An elution profile is recorded by means of an LKB 2210 recorder which runs at a velocity of 1 mm/minute. The absorption is measured at 280 nm by means of an LKB 2238 UVICOR S II. The recorded elution profile from this first elution step is indicated at FIG. 1. In FIG. 1, it can be observed that all of the fractions containing primarily dimeric forms of lysozyme are indicated by shading under the thick line. The salt gradient is indicated by the thin line.

The protein mixture of each individual fraction was analyzed by an SDS-polyacrylamide gel-electrophoresis (PAGE) in accordance with the procedures of Thomas et al, PNAS 72: 2626 (1975). For that purpose, 50 μl of each fraction was mixed with 50 μl of a coating buffer and was heated for 10 minutes at 95° C. Next, 25 μl of this mixture are spread in a gel pocket. The protein mixture Standard IV (Merck) was applied as a reference. The coating buffer was comprised of the following ingredients:

0.72 g tris HCl (0.06 M)

0.136 g EDTA (III) (5 mM)

0.18 g glycerine (10%)

5 g SDS (5%)

pH adjusted to 7.2 (add 90 ml $H_2O$)

10 ml beta-mercaptoethanol (10%)

For the gel-electrophoresis, an 18% separating gel is prepared which is layered over with a 3.9% collecting gel. The separating gel solution for 18% acrylamide was comprised of the following:

9 g acrylamide 0.045 g bis-acrylamide 0.136 g tris HCl pH 8.8 (0.325 M)

0.03 g SDS

200 μl 10% ammonium persulfate solution

20 μl TEMED

The collecting gel solution for 3.9% acrylomide had the following ingredients:

0.39 g acrylamide 10.4 mg bis-acrylamide 10 mg SDS

100 μl 10% ammonium persulfate solution

10 μl TEMED

The SDS-polyacrylamide gel was prepared by taking two 20×20 cm glass plates, which are thoroughly cleaned and rinsed with ethanol, and placing them one atop the other. Two spacing strips of 1 mm thickness (length 20 cm, breadth 1 cm) provided the space between the plates into which the gel was poured. The spacing strips are mounted on the left and right edges of the glass plates. The bottom edge is sealed by a textile adhesive strip, and all three edges are reinforced with clamps. The edges are additionally sealed with a 1% agarose solution. After hardening of the agarose, the separating gel solution prepared above is filled into the interstices in vertical position up to approximately 3 cm below the top edge of the glass plate, and with the aid of a Pasteur pipette is overlaid with a layer of water. The gel is polymerized after approximately 30 minutes. The coating of water is poured off, and the edge of the gel is rinsed one time with the collecting gel solution described above.

Next, the collecting gel solution is filled in up to the edge, and a Teflon sample collecting comb is put in so that the bottom edge of the sample pocket lies approximately 1 cm over the front edge of the separating gel layer. After approximately 15 minutes, the collecting gel is polymerized, and the comb can be removed. Next, the textile adhesive strip is removed and the gel is joined in the vertical position to an electrophoresis apparatus. The buffer chambers are filled with an electrophoresis buffer (eg tris-base(0.05 M); 28.5 g glycine(0.38 M); 1 g SDS(0.1%); and 1,000 ml $H_2O$) and the gel pockets are rinsed once with the aid of a buffer spray. The lysozyme dimer samples are heated for approximately 10 minutes in the buffer coating at 95° C. and filled into a container or area in the testing sample pocket corresponding the gel pocket.

The electrophoresis was carried out at about 20 mA for about 4 hours. If overnight electrophoresis is desired however, this could be carried out at a reduced charge of about 6–8 mA. The moving front is made visible by intermixing of 0.02% bromophenol-blue into the coating buffer. The electrophoresis was terminated when the moving front of the process reached the bottom edge of the gel. The separating gel is cut out, dyed for approximately 30 minutes in a fixing solution and is then bleached again for 2 hours in a bleaching solution of 400 ml methanol, 140 ml acetic acid, and 2,000 ml $H_2O$. The fixing solution was prepared by combining 500 ml of the bleach solution with 12 ml of a dye solution comprising 1 g Coomassie-blue (R250, Merck), 50 ml $H_2O$, and 50 ml methanol. The protein bands were then made visible by coloring with the dye solution as indicated above. The traces made using the SDS-PAGE technique indicated a gradual increase in the amount of dimerized lysozyme in the samples which ultimately included fractions containing multimers as well. The fractions which were primarily lysozyme in the dimeric form were collected and were concentrated down to 800 ml in a tangential flow system. This system, manufactured by Millipore, included a filtron exclusive 10,000 d filter, an olefin membrane having a tear resistance of 7 bar, and a Verder 80 W (Type 20–30 No. 60079) pump. The input pressure was 2 bar, and the output pressure was at the minimum lower than 0.2. The working capacity was approximately 1 liter/hour. The apparatus has a dead volume of 400 ml so that upon termination, when the membrane is rinsed with 400 ml, a total volume of 1200 ml is obtained.

The lysozyme dimers were then purified by filtration in a Sephadex G 50 F (Pharmacia) ion exchanger. For that, a column (diameter 25.2 cm, height 120 cm) was equilibrated with a volume of 60 liters with 5 mM of an ammonium acetate buffer at pH 5. The total protein solution of 1.2 liters was coated on and eluted at a flow rate of 70 ml/minute in the equilibrium buffer. Fractions of approximately 700 ml were collected, and each 50 ul per fraction was analyzed as described above using the SDS-PAGE procedure.

Figure 2:
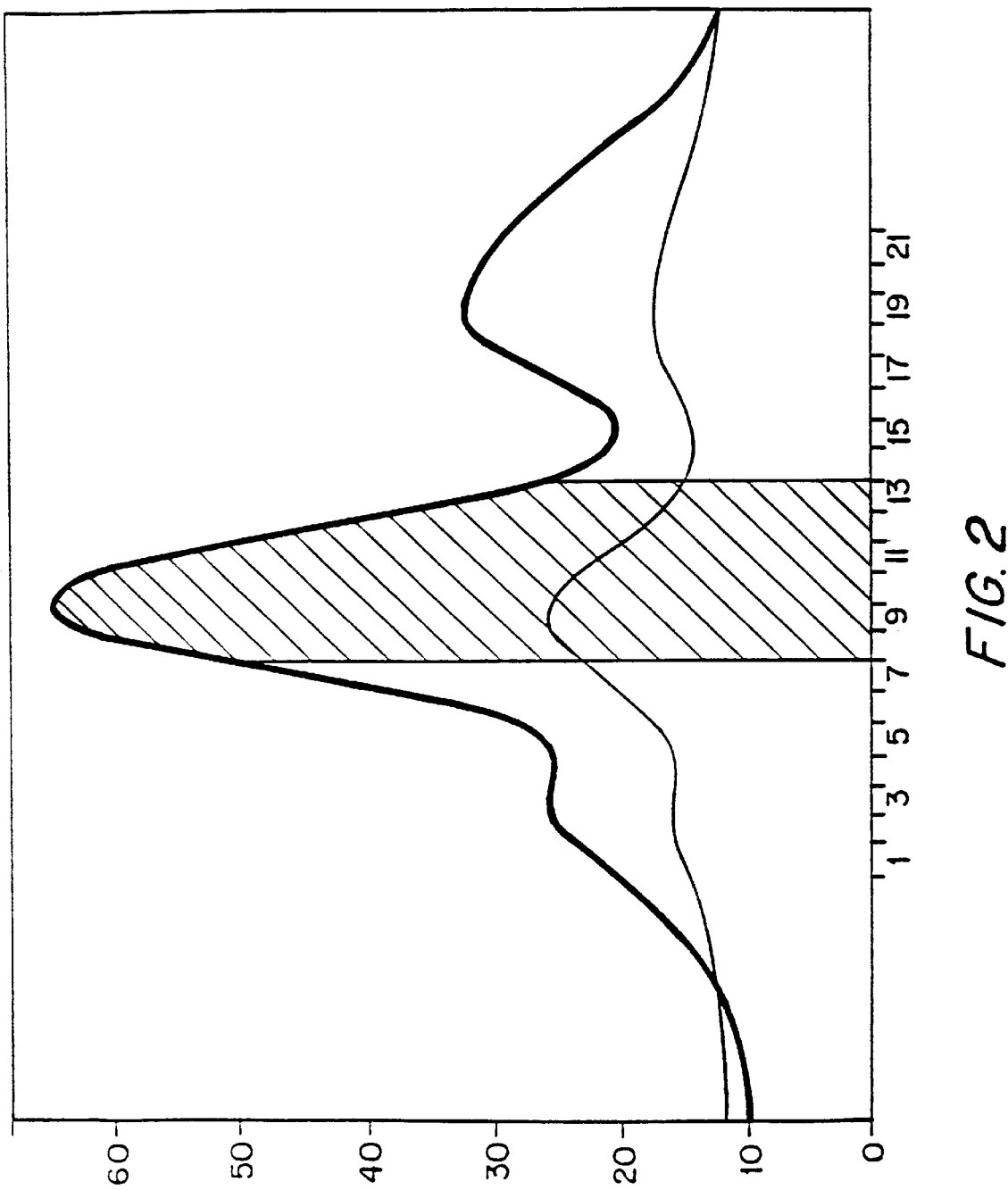
FIG. 2 is a graphic representation of the elution profile obtained from the second elution step carried out in accordance with the present invention.

The elution profile for this filtration procedure was indicated by a recorder having a velocity of 0.5 mm/minute measuring the absorption at 280 nm. The recorded elution profile is indicated at FIG. 2. The thick line in FIG. 2 represents the absorption profile of the lysozyme solutions with more sensitive detection than in the thin line of the graph. Although this elution profile shows three peaks, it is the middle peak which is extremely prominent, and this peak represents the dimer fractions. The first and last peaks referred to the lesser amounts of multimeric and monomeric forms of lysozyme remaining in the coating mixture.

Finally, the fractions containing highly purified lysozyme dimer (fractions 8–13 in the elution profile) are collected and are concentrated with the tangential flow system described above. After concentration, the purified dimer is then lyophilized. After repeating this process several times, individual batches of dimer are purified, placed in distilled water, and then are again lyophilized, so that a homogenous charge of lysozyme diner is obtained.

EXAMPLE 2

Enzyme Activity Test

The enzyme activity of the dimeric lysozyme prepared in the present invention can be tested using an activity test described in Verhamme et al, *International Pharmacy Journal*, Vol. 2:5 (1988). This test is based on reducing the microorganism *Micrococcus luteus* into soluble decomposition products by enzyme-induced lysis of the microorganism's cell walls. The gradual lightening or total elimination of the turbidity at a wavelength of 450 nm is measured by a spectral photometer as a measure of the enzyme activity.

For this test, a suspension of *Micrococcus luteus* was prepared. Approximately 30 mg of *M.luteus* (ATCC 4698, living, lyophilized, produced by Boehringer Mannheim) is ground, transferred with approximately 25 ml of a phosphate buffer into a 100 ml Erlenmeyer flask, and stirred slowly for approximately 2 hours at room temperature using a magnetic stirrer. Next, the suspension is centrifugated for 1 minute at 500 rpm, and the excess is decanted into a fresh vessel. Small lumps of bacteria which are not suspended are found in the sediment. The suspension is stirred further, and in order to prevent sedimentation, is diluted with phosphate buffer. It is measured in comparison with air, and the layer of thickness is 1 cm. Corresponding representative samples of the suspension diluted in this manner with continuous stirring are taken out for the test measurements.

Sample solutions containing the lysozyme dimer are prepared in a concentration of 1 mg/ml of water. The test sample is dissolved in water immediately before the measurement is to take place, and the activity is correspondingly diluted to 1:250 or 1:25 in distilled water. The test is then carried out at a constant temperature of 25° C. For this purpose, all of the solutions must be at 25° C., and the measurement is undertaken using a temperature-controlled cuvette. The cuvette volume is 3 ml, the thickness of the layer of the test solution is 1 cm, and the decrease in turbidity following the start of the reaction is measured at 450 nm over 7 minutes. The turbidity decrease per minute is indicated in a spectral photometer (Spectronic 1001, Bausch & Lomb). The reaction mixture was made from 2.95 ml of the *M.luteus* suspension and 0.05 ml of the test sample solution. Each measurement was repeated twice and an average value determined therefrom.

The rate of enzyme activity as determined by the turbidity decrease is tracked starting from the linear initial range, and a $\Delta E$ (E=extinction of the bacteria)/minute time period is analyzed. The value of $\Delta E$/minute is smaller than 0.03, and the decree of dilution of the test sample must be selected correspondingly. The turbidity decrease is also determined in a blank sample test (*M.luteus* with water), and the value which is generated through the cuvette must be drawn from the measured values of the test samples.

The tests carried out indicated a significant amount of enzyme activity in the *M.luteus* suspension with dimer solution which was not observed in the control sample of *M.luteus* suspension with water.

What is claimed is:

1. A purified lysozyme dimer which does not contain monomeric or multimeric forms of lysozyme or other contaminants.

2. A lysozyme dimer purified to a purity resulting from the purification steps of:

(a) preparing a lysozyme solution by adding monomeric lysozyme to a buffer solution and adjusting the pH to at least 9;

(b) adding a suberimidate coupling reagent to dimerize the lysozyme monomers in the lysozyme solution while maintaining the pH at at least 9;

(c) stopping the dimerization reaction by lowering the pH to 7;

(d) purifying the dimerized lysozyme solution by carrying out a first elution step in which the solution is eluted through an ion exchange column, and collecting the fractions which are substantially comprised of the dimeric form of lysozyme;

(e) filtering the collected fractions from the first elution step by carrying out a second elution step in which the collected fractions from the first step are eluted through a second ion exchange column; and (f) collecting the highly purified dimeric lysozyme product resulting from the second elution step.

* * * * *